（12）United States Patent
Yi et al.

(10) Patent No.: US 8,535,335 B2
(45) Date of Patent: Sep. 17, 2013

(54) NEEDLE-COUPLED PARALLEL MECHANISM

(75) Inventors: Byung-Ju Yi, Gyeonggi-do (KR); Hoon Lim, Gyeonggi-do (KR); Sang-Heon Lee, Gyeonggi-do (KR)

(73) Assignee: IUCF-HYU (Industry-University Cooperation Foundation Hanyang University), Seoul (KR)

( * ) Notice: Subject to any disclaimer, the term of this patent is extended or adjusted under 35 U.S.C. 154(b) by 346 days.

(21) Appl. No.: 12/759,101

(22) Filed: Apr. 13, 2010

(65) Prior Publication Data

US 2011/0251624 A1    Oct. 13, 2011

(51) Int. Cl.
*A61B 19/00*    (2006.01)

(52) U.S. Cl.
USPC ........... 606/130; 606/250; 606/251; 606/252; 606/256; 74/48; 600/139; 600/417; 600/429; 128/121.1

(58) Field of Classification Search
USPC ............... 606/130, 246, 250, 251, 252, 256, 606/254; 74/839, 840, 43, 42, 48; 128/121.1, 128/123.1; 600/139, 206, 417, 429
See application file for complete search history.

(56) References Cited

U.S. PATENT DOCUMENTS

| 5,931,810 A * | 8/1999 | Grabek .................. 604/506 |
| 6,030,386 A * | 2/2000 | Taylor et al. ............ 606/56 |
| 2005/0049486 A1* | 3/2005 | Urquhart et al. ......... 600/429 |
| 2005/0156877 A1* | 7/2005 | Schaeffer ............... 345/156 |

* cited by examiner

*Primary Examiner* — Gary Jackson
*Assistant Examiner* — Sidharth Kapoor
(74) *Attorney, Agent, or Firm* — Womble Carlyle Sandridge & Rice, LLP

(57) ABSTRACT

A needle-coupled parallel mechanism is provided. The needle-coupled parallel mechanism is structurally improved so as to have a broad working area and a high precision. The needle-coupled parallel mechanism comprises a fixedly positioned frame, a main shaft, three first links, three second links, and a needle. The main shaft is arranged so as to be movable relative to the frame. One end of each of the first links is connected to the frame between both ends of the main shaft and the other end thereof is connected to one end of the main shaft. One end of each of the second links is connected to the frame between both ends of the main shaft and the other end thereof is connected to the other end of the main shaft. The needle is linearly movably coupled to the main shaft to perform a predetermined operation on a target object. Each of the first links and the second links has at least three joints selected from a prismatic joint, a 1-axis revolute joint, a 2-axis revolute joint and a spherical joint. The needle and the main shaft are moved with 6 degrees-of-freedom in conjunction with the operations of the first links and the second links.

10 Claims, 8 Drawing Sheets

U=[0, 0, 0.4, 0°, 0°, 0°]

U=[0, 0, 0.4, 10°, 10°, 0°]

NEEDLE-COUPLED PARALLEL MECHANISM

BACKGROUND OF THE INVENTION

1. Field of the Invention

The present invention relates to a needle-coupled parallel mechanism that performs an operation on a target object while controlling its position and posture in a three-dimensional space.

2. Description of the Related Art

In recent years, many medical devices have been developed for various medical purposes, for example, biopsy and drug infusion into living bodies. A typical example of such medical devices consists of a needle inserted into a living body to perform a medical function, such as drug infusion or tissue sampling, and a mechanism coupled to the needle to control the posture and position of the needle.

The size of and the precision in the working area of the medical device are important factors in determining the performance of the medical device. The size of the working area means the size of the area where the position and posture of the needle are controllable, and the precision in the working area means how precisely the needle is controlled in the working area. Since the position and posture of the needle are controlled by the mechanism, a broad working area and a high precision of the mechanism are also required in order to improve the performance of the medical device.

Serial mechanisms have been usually used in medical devices. Such a serial mechanism includes a plurality of links connected in series with each other. The serial mechanism has many problems despite the advantage of a broad working area. For example, the needle reflects cumulative errors generated in the respective links in the course of controlling the posture and position of a needle, resulting in a very low precision of the serial mechanism. Further, the links coupled in series inevitably increase the size and inertial mass of the serial mechanism, which greatly increases the force necessary to control the posture and position of the needle.

Thus, there is a need to develop a new type of mechanism that can control the posture and position of a needle with a small force while possessing a broad working area and a high precision.

SUMMARY OF THE INVENTION

The present invention has been made in view of the above problems, and it is an object of the present invention to provide a structurally improved needle-coupled parallel mechanism that has a broad working area and a high precision.

To achieve the object of the present invention, there is provided a needle-coupled parallel mechanism which comprises a fixedly positioned frame, a main shaft arranged so as to be movable relative to the frame, three first links, each of which has one end connected to the frame between both ends of the main shaft and the other end connected to one end of the main shaft, three second links, each of which has one end connected to the frame between both ends of the main shaft and the other end connected to the other end of the main shaft, and a needle linearly movably coupled to the main shaft to perform a predetermined operation on a target object, wherein each of the first links and the second links has at least three joints selected from a prismatic joint, a 1-axis revolute joint, a 2-axis revolute joint and a spherical joint, and the needle and the main shaft are moved with 6 degrees-of-freedom in conjunction with the operations of the first links and the second links.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
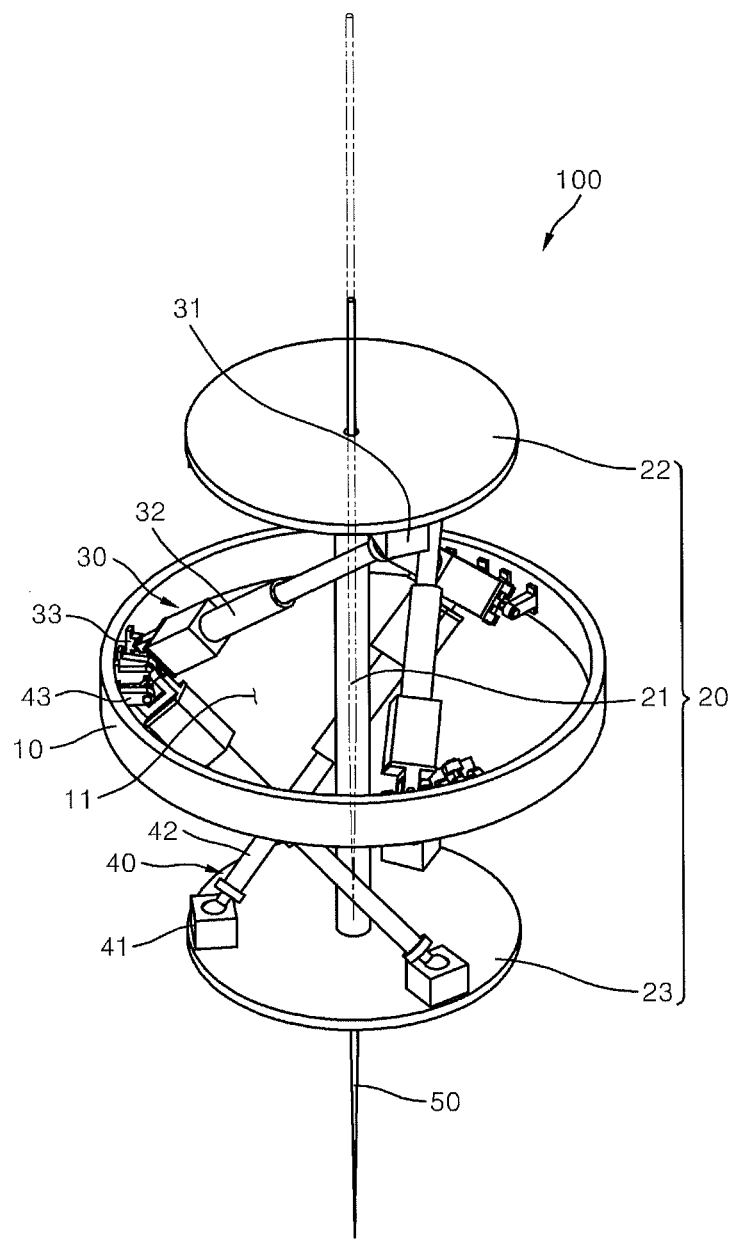
FIG. 1 is a perspective view of a needle-coupled parallel mechanism according to an embodiment of the present invention.
Figure 2:
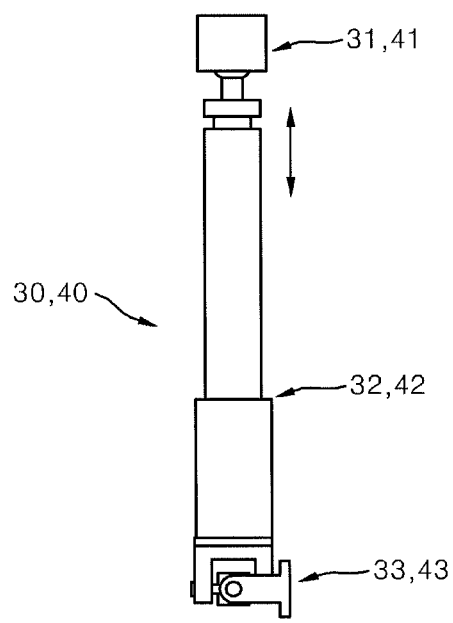
FIG. 2 is a conceptual view of a first link or a second link of the needle-coupled parallel mechanism of FIG. 1.
Figure 3:
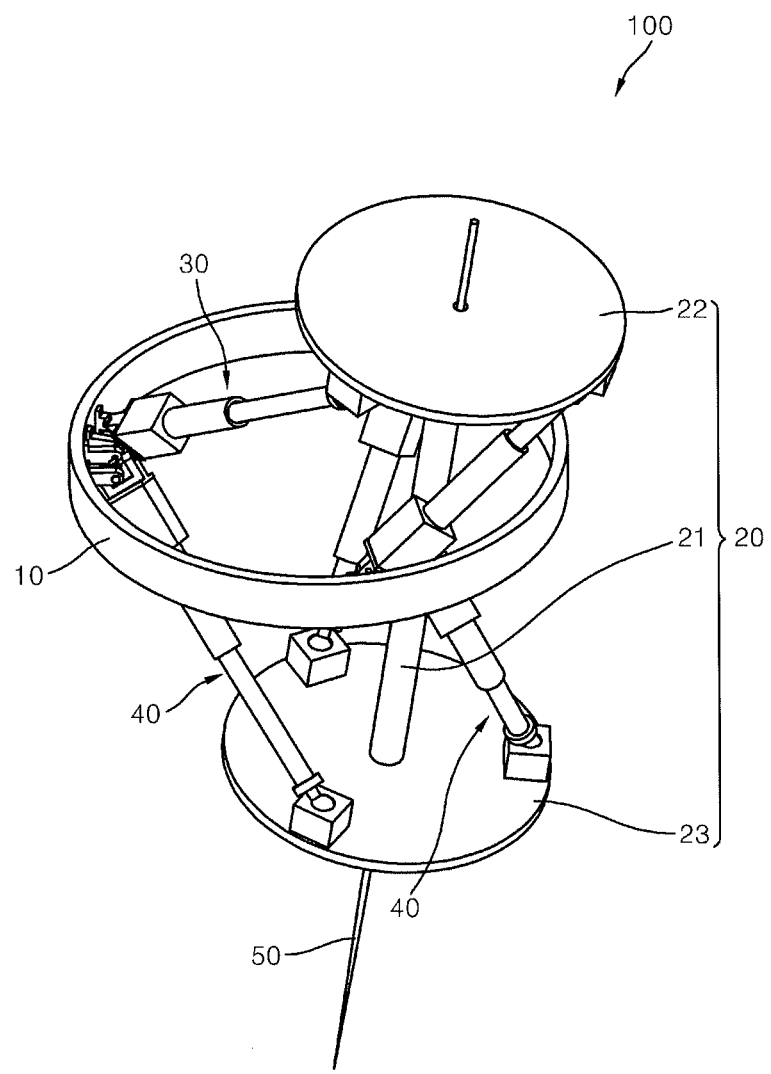
FIGS. 3 and 4 are perspective views for explaining the operation of the needle-coupled parallel mechanism of FIG. 1.
Figure 4:
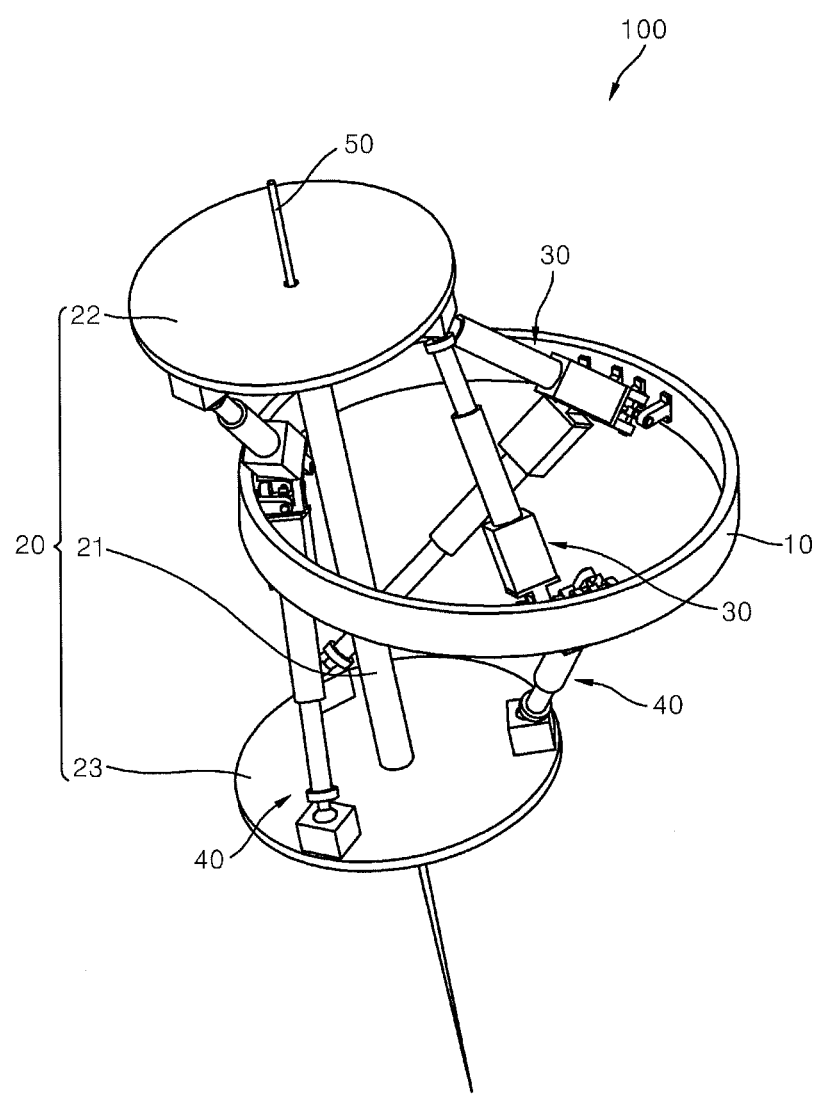

FIG. 1 is a perspective view of a needle-coupled parallel mechanism according to an embodiment of the present invention, FIG. 2 is a conceptual view of a first link or a second link of the needle-coupled parallel mechanism, and FIGS. 3 and 4 are perspective views for explaining the operation of the needle-coupled parallel mechanism.

Referring to FIGS. 1 through 4, the needle-coupled parallel mechanism 100 comprises a parallel mechanism and a needle 50 coupled to the parallel mechanism.

The parallel mechanism serves to control the posture and position of the needle 50. The parallel mechanism includes a frame 10, a main shaft 20, first links 30, and second links 40.

One end of each of the first links 30 and the second links 40 is fixed to the frame 10. An explanation of the first links 30 and the second links 40 will be provided below. No limitation is imposed on the shape of the frame 10 so long as one end of each of the first links 30 and the second links 40 can be fixedly connected to the frame 10. In this embodiment, the frame 10 is in the shape of a circular ring and has a through-hole 11 formed in the center portion thereof.

The position and posture of the main shaft 20 in a three-dimensional space are controlled by the mechanism. The main shaft 20 is arranged so as to be movable relative to the frame 10. The main shaft 20 includes a shaft body 21, a first extension 22 and a second extension 23. The shaft body 21 is elongated in one direction and inserted into the through-hole 11 of the frame 10. The first extension 22 extends from the upper end of the shaft body 21 in a direction crossing the longitudinal direction of the shaft body 21. The second extension 23 extends from the lower end of the shaft body 21 in a direction crossing the longitudinal direction of the shaft body 21. In this embodiment, the first extension 22 and the second extension 23 are in the shape of disk shapes that extend from the circumferences of the upper end and the lower end of the shaft body 21, respectively, in a direction perpendicular to the longitudinal direction of the shaft body 21. The first extension 22 and the second extension 23 are arranged parallel to each other. An insertion hole penetrating the shaft body 21, the first extension 22 and the second extension 23 is formed in the center portion of the main shaft 20. The needle 50 is inserted into the insertion hole, as described below.

The first links 30 and the second links 40 serve to control the position and posture of the main shaft 20. Each of the first links 30 and the second links 40 has at least three joints selected from a prismatic joint, a 1-axis revolute joint, a 2-axis revolute joint and a spherical joint. The prismatic joint is a joint that is extendable in one axial direction. A linear actuator is used as the prismatic joint. The 1-axis revolute joint refers to a pin joint that is rotatable about one rotational axis. The 2-axis revolute joint refers to a joint that is rotatable in two directions about two rotational axes. A universal joint is used as the 2-axis revolute joint. The spherical joint refers to a joint that is rotatable in three directions about three rotational axes. A ball-socket joint is used as the spherical joint.

In this embodiment, each of the first links 30 and the second links 40 consists of a spherical joint 31 or 41, a prismatic joint 32 or 42, and a 2-axis revolute joint 33 or 43, as illustrated in FIG. 2. The spherical joints 31 and 41 and the 2-axis revolute joints 33 and 43 are driven joints. The prismatic joints 32 and 42 are driving joints, each of which is extended by means of a driving source (e.g., a motor) connected thereto. The prismatic joints 32 and 42 provide driving forces to control the posture and position of the main shaft 20, which will be described below.

One end (i.e. the 2-axis revolute joint 33) of each of the three first links 30 is connected to the frame 10. The other end (i.e. the spherical joint 31) of each of the first links 30 is connected to the other end (i.e. the first extension 22) of the main shaft 20. The three 2-axis revolute joints 33 are arranged at equal intervals along the inner circumference of the frame 10 to form a regular triangle. The three spherical joints 31 are arranged at equal intervals in the circumferential direction of the first extension 22 to form a regular triangle.

One end (i.e. the 2-axis revolute joint 43) of each of the three second links 40 is connected to the frame 10. The other end (i.e. the spherical joint 41) of each of the second links 40 is connected to the other end (i.e. the second extension 23) of the main shaft 20. The three 2-axis revolute joints 43 are arranged at equal intervals between the respective 2-axis revolute joints 33 of the first links 30 along the inner circumference of the frame 10 to form a regular triangle. The portion (i.e. the first extension 22) of the main shaft 20 to which the spherical joint 31 of each of the first links 30 is connected and the portion (i.e. the second extension 23) of the main shaft 20 to which the spherical joint 41 of each of the second links 40 are arranged parallel to each other.

The needle 50 is a part that performs a predetermined operation on a target object. The needle 50 may have various shapes depending on the intended applications. An explanation of the shape of the needle suitable for biopsy will be given first, and then other shapes of the needle will be explained.

The needle 50 is made of a material harmless to humans/animals because it is directly inserted into a living body. The needle 50 is elongated in the longitudinal direction of the shaft body 21. The needle has a sharp tip so as to be easily inserted into a living body. The needle 50 is linearly movably coupled to the main shaft 20. In this embodiment, the needle 50 is inserted into the insertion hole of the main shaft 20. When the needle 50 is moved upward as indicated by an imaginary line in FIG. 1, the lower end of the needle is embedded within the main shaft 20. When the needle 50 is moved downward as indicated by a solid line in FIG. 1, the lower end of the needle protrudes outwardly from the main shaft and is inserted into a living body (not shown) to sample a living tissue. A driving source is connected to the needle 50.

The driving source acts to move the needle 50 linearly. The driving source may employ various known constructions, for example, a ball-screw mechanism and a motor for driving the mechanism, which are not described in particular detail in order to avoid unnecessarily obscuring the features of the present invention.

When it is intended to use the needle-coupled parallel mechanism as a medical device for injecting a drug into a living body, the needle is formed so as to have a hollow through which the drug supplied from the outside is injected into the living body after it is inserted into the living body.

Alternatively, the needle-coupled parallel mechanism may be used as a medical device for applying an electrical shock (i.e. a current) to a particular site of a living body. In this case, the needle is elongated in one direction and has a sharp tip so as to be easily inserted into the living body. The needle is made of an electrically conductive material through which an externally applied current can easily be delivered to the living body. The portion of the needle other than the tip is surface-treated with an insulating material such that the electrical shock is applied to only the target site of the living body when the needle is in contact with the needle tip.

A state in which the prismatic joints 32 and 42 are extended in small increments to rotate the main shaft 20 at an angle of about 85° relative to the vertical axis (i.e. a state in which the main shaft 20 is twisted) is set to the initial state illustrated in FIG. 1. In this state, a relatively small singularity is created, which ensures the broadest work space. When the prismatic joints of the first links 30 and the second links 40 are suitably extended in the initial stage illustrated in FIG. 1, the 2-axis revolute joints and the spherical joints are rotated depending on variations in the relative length of the first links 30 and the second links 40. These rotations lead to 6 degrees-of-freedom motion of the main shaft 20 and the needle 50 coupled thereto in a three-dimensional space, and as a result, the postures and positions of the main shaft 20 and the needle 50 are changed to those illustrated in FIGS. 3 and 4. In conclusion, the position and posture of the needle 50 can be controlled by suitably extending the prismatic joints. In the state in which the position and posture of the needle 50 are controlled as desired, the needle 50 is moved downward and inserted into a target site (i.e. a site to be examined) of a human body.

The use of the parallel mechanism of this embodiment enables control of the position and posture of the needle 50 with a smaller force than the use of a conventional serial mechanism because parallel mechanism of this embodiment has a smaller inertial mass than a conventional serial mechanism. In addition, the needle of the parallel mechanism of this embodiment reflects averages of errors generated in the respective links in the course of controlling the posture and position of the needle, whereas a needle of a serial mechanism reflects cumulative errors generated from respective links in the course of controlling the posture and position of the needle. Therefore, the parallel mechanism of this embodiment can control the position and posture of the needle much more precisely than a serial mechanism. Furthermore, the serial connection of the links of the parallel mechanism according to this embodiment enables manufacture of the parallel mechanism in a size smaller than the size of a serial mechanism. In conclusion, the needle-coupled parallel mechanism 100 of this embodiment can be precisely controlled with a small force and can be reduced in size, compared to conventional serial mechanisms.

On the other hand, the parallel mechanism 100 of this embodiment is distinguishable from a parallel mechanism, such as a Stewart platform, in terms of its structure. Specifically, the main shaft 20 is inserted into the frame 10, the first extension 22 of the main shaft 20 is positioned over the frame 10, the second extension 23 of the main shaft 20 is positioned below the frame 10, the three first links 30 arranged on the frame 10 to connect between the frame 10 and the first extension 22 are extendable upwardly from the frame 10, and the three second links 40 arranged under the frame 10 to connect between the frame 10 and the second extension 23 are extendable downwardly from the frame 10. The first links 30 and the second links 40 arranged so as to be extendable in different directions facilitate the delivery of forces to the main shaft. In addition, the singularity of the parallel mechanism 100 is decreased as compared to a general parallel mechanism, resulting in an increase in the work space of the needle 50 coupled to the main shaft 20.

Figure 5:
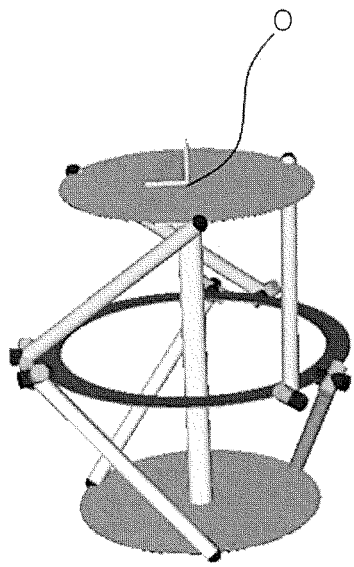
FIGS. 5 and 6 show the work spaces of a main shaft of the needle-coupled parallel mechanism of FIG. 1 according to the initial position and posture of the main shaft, as represented three-dimensionally using a simulator.
Figure 5:
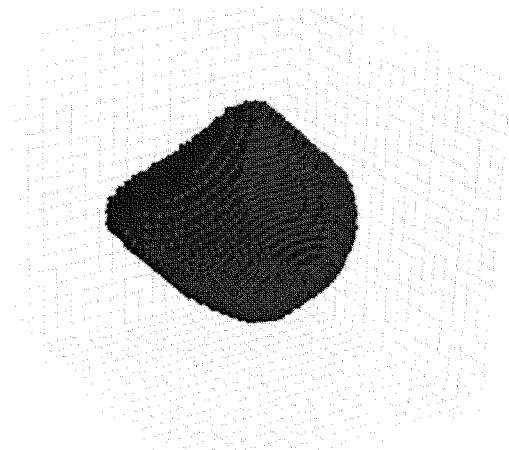
Figure 6:
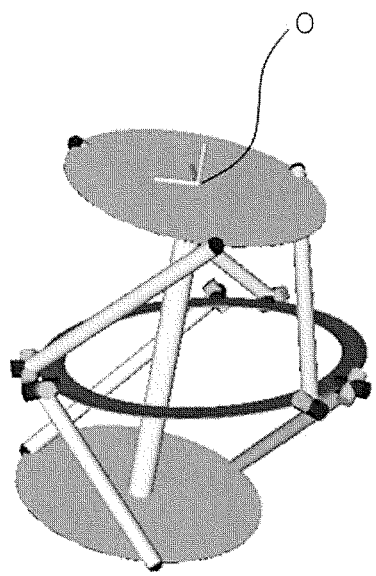
Figure 6:
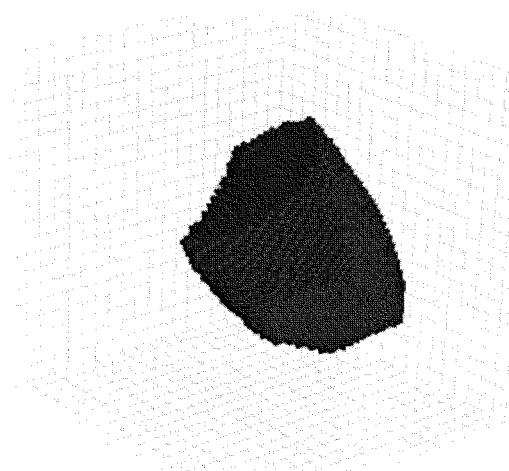

FIGS. 5 and 6 show the work spaces of the main shaft according to the initial position and posture ("U") of the main shaft, as represented three-dimensionally using a simulator. Specifically, FIGS. 5 and 6 show results regarding the work spaces of the main shaft depending on the initial position and posture ("U") of the center point O of the first extension of the main shaft 20. Since the needle 50 is operated with the main shaft 20, the work space of the main shaft can be considered the same as that of the needle 50 (the work spaces of the center point O and the needle 50 are only moved parallel to each other on the coordinates, and the shapes and sizes thereof are the same). The posture ("U") is a vector consisting of six elements, i.e. the X, Y and Z coordinates and the rotational angles with respect to the X, Y and Z axes.

Referring to FIGS. 5 and 6, it can be confirmed that the work space region is varied depending on the posture ("U") of the reference point O. The simulation results also confirm that no singularity is generated in the work space.

Many modifications are possible to the construction of the first links and the second links. For example, FIGS. 7 through 9 are conceptual views illustrating some embodiments of the first or second link.

Figure 7:
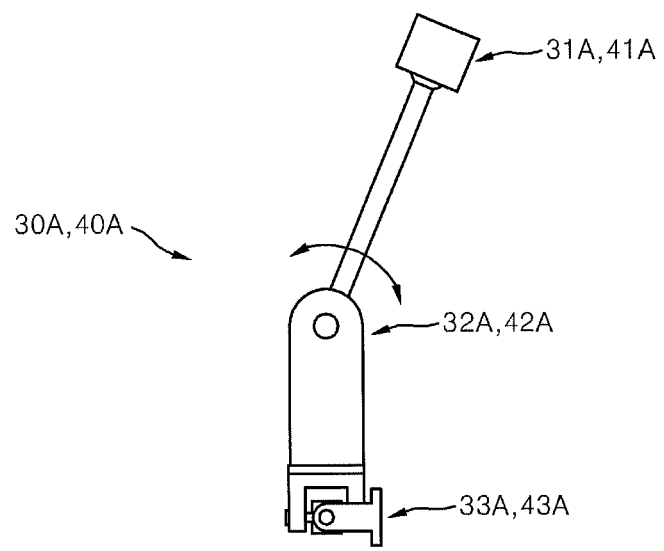
FIGS. 7 to 9 are conceptual views illustrating some embodiments of the first or second link of the needle-coupled parallel mechanism of FIG. 1.

A first link 30A or a second link 40A illustrated in FIG. 7 has a 2-axis revolute joint 33A or 43A, a 1-axis revolute joint 32A or 42A and a spherical joint 31A or 41A. The 2-axis revolute joint 33A or 43A and the spherical joint 31A or 41A are driven joints and are connected to the frame and the main shaft, respectively. The 1-axis revolute joint 32A or 42A is a driving joint to which a driving source (e.g., a motor) is connected. The 1-axis revolute joint is rotated by the movement of the driving source to provide a driving force for controlling the posture and position of the main shaft.

Figure 8:
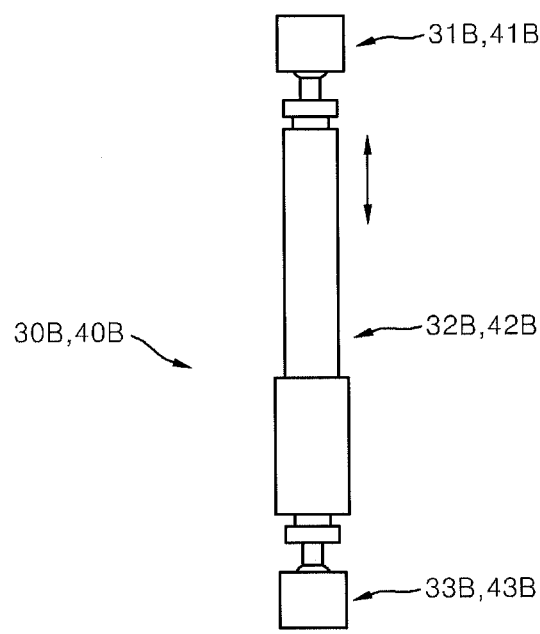

A first link 30B or a second link 40B illustrated in FIG. 8 has a spherical joint 33B or 43B, a prismatic joint 32B or 42B and a spherical joint 31B or 41B. The pair of spherical joints 33B or 43B and 31B or 41B are driven joints and are connected to the frame and the main shaft, respectively. The prismatic joint 32B or 42B is a driving joint to which a driving source (e.g., a motor) is connected. The prismatic joint is extended by the movement of the driving source to provide a driving force for controlling the posture and position of the main shaft.

Figure 9:
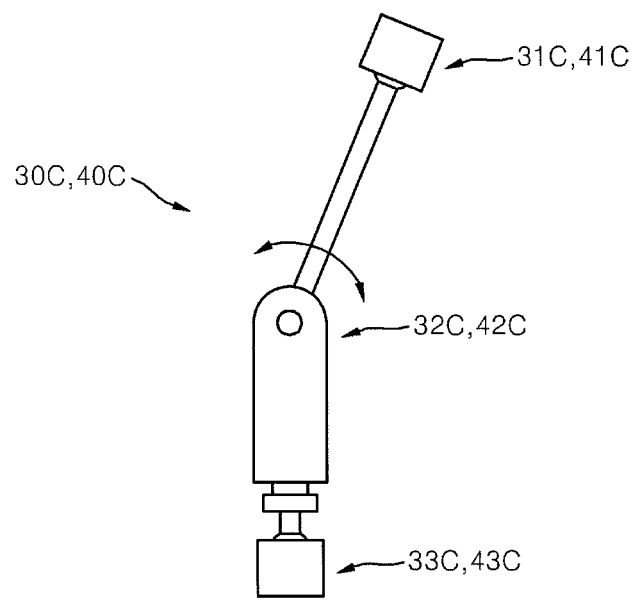

A first link 30C or a second link 40C illustrated in FIG. 9 has a spherical joint 33C or 43C, a 1-axis revolute joint 32C or 42C and a spherical joint 31C or 41C. The pair of spherical joints 33C or 43C and 31C or 41C are driven joints and are connected to the frame and the main shaft, respectively. The prismatic joint 32B or 42B is a driving joint to which a driving source (e.g., a motor) is connected. The 1-axis revolute joint is extended by the movement of the driving source to provide a driving force for controlling the posture and position of the main shaft.

Figure 10:
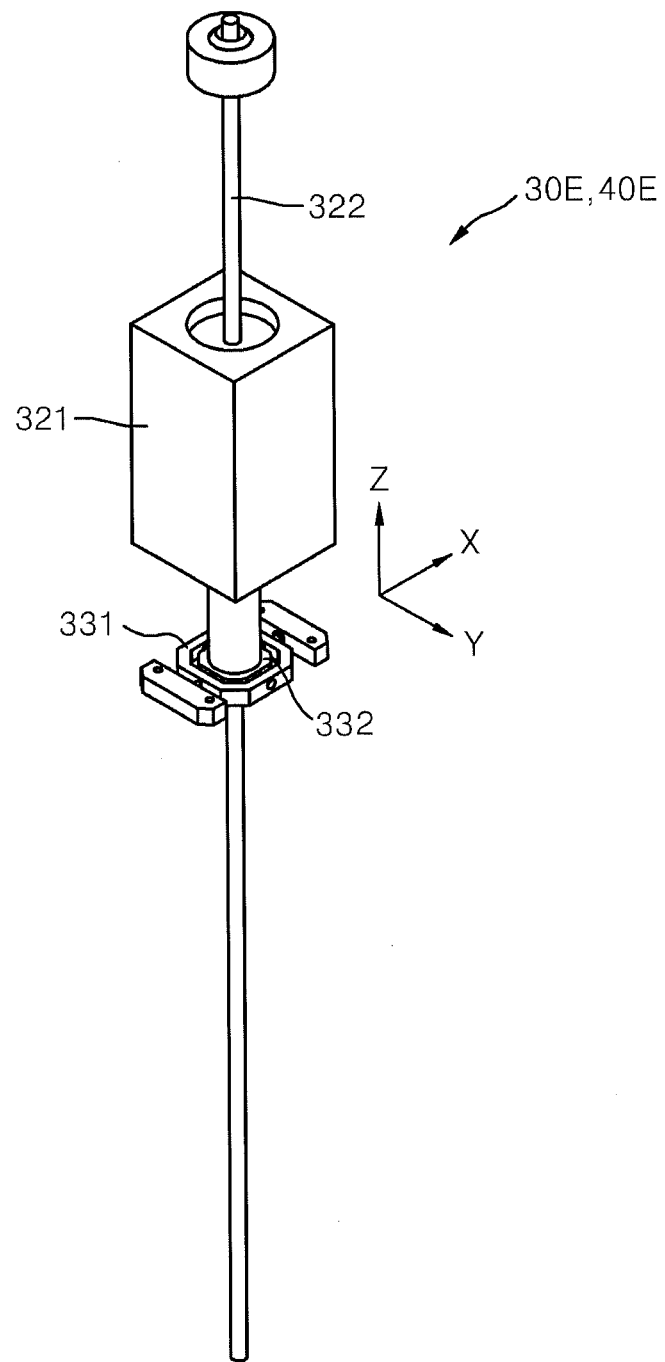
FIG. 10 is a perspective view illustrating another embodiment of the first or second link of the needle-coupled parallel mechanism of FIG. 1.

In another embodiment, the first links and the second links can be constructed as illustrated in FIG. 10. A first link 30E or a second link 40E illustrated in FIG. 10 has a 2-axis revolute joint, a prismatic joint and a spherical joint. The 2-axis revolute joint (e.g., a universal joint) has a first rotating plate 331 rotatable about the X axis as a rotation axis and a second rotating plate 332 positioned in the first rotating plate 331 and rotatable about the Y axis as a rotation axis. The second rotating plate 332 is formed with a through-hole. The prismatic joint (e.g., a linear actuator) has a housing 321 and a screw 322. The housing 321 is coupled to the second rotating plate 332 of the 2-axis revolute joint. The screw 322 is inserted into the housing 321 and the through-hole of the second rotating plate 332. The screw 322 is moved linearly relative to the housing 321 in conjunction with the movement of a motor (not shown) installed in the housing.

According to the foregoing embodiment, the extendable length of the prismatic joint is limited to the length of the screw inserted into the housing. In contrast, according to this embodiment, the extendable length of the prismatic joint can be further increased because the screw 322 passes through the second rotating plate 332. The increased length of the prismatic joint increases the allowable displacement of the main shaft, leading to an increase in the work space of the main shaft.

Although the present invention has been described herein with reference to the forgoing preferred embodiments, these embodiments do not serve to limit the scope of the invention. Accordingly, those skilled in the art will appreciate that various modifications and variations are possible without departing from the spirit and scope of the present invention as set forth in the appended claims. Such modifications and variations are intended to come within the scope of the appended claims.

For example, the driving source provided to linearly move the needle in this embodiment can be omitted. That is, the needle can be manually moved linearly without the need for any driving source.

As is apparent from the above description, the needle-coupled parallel mechanism of the present invention has a broad working area and a high precision. In addition, the needle-coupled parallel mechanism of the present invention can control the position and posture of the needle with a small force. Furthermore, the needle-coupled parallel mechanism of the present invention can be reduced in size.

What is claimed is:
1. A needle-coupled parallel mechanism, comprising:
a fixedly positioned frame having an upper and lower surface;
a main shaft arranged so as to be movable relative to the frame, the main shaft having opposing ends and the frame being disposed between the opposing ends of the main shaft;
three first links, each of which has one end connected to the frame and the other end extending above the upper surface of the frame and connected to one of the opposing ends of the main shaft;
three second links, each of which has one end connected to the frame and the other end extending below the lower surface of the frame and connected to the other of the opposing ends of the main shaft; and
a needle linearly movably coupled to the main shaft to perform a predetermined operation on a target object, wherein each of the first links and the second links has at least three joints selected from the group consisting of a prismatic joint, a 1-axis revolute joint, a 2-axis revolute joint and a spherical joint, and the needle and the main shaft are moved with 6 degrees-of-freedom in conjunction with the operations of the first links and the second links.

2. A needle-coupled parallel mechanism, comprising:

a fixedly positioned frame;

a main shaft arranged so as to be movable relative to the frame, the main shaft having opposing ends and the frame being disposed between the opposing ends of the main shaft;

three first links, each of which has one end connected to the frame and the other end extending outwardly of the frame and connected to one of the opposing ends of the main shaft;

three second links, each of which has one end connected to the frame and the other end extending outwardly of the frame and connected to the other of the opposing ends of the main shaft; and a needle linearly movably coupled to the main shaft to perform a predetermined operation on a target object, wherein each of the first links and the second links has at least three joints selected from the group consisting of a prismatic joint, a 1-axis revolute joint, a 2-axis revolute joint and a spherical joint, and the needle and the main shaft are moved with 6 degrees-of-freedom in conjunction with the operations of the first links and the second links, wherein the frame defines a through-hole and the main shaft extends through the through-hole so as to be movable relative to the frame, wherein the main shaft has an elongated shaft body, a first extension extending from one end of the shaft body in a direction crossing the longitudinal direction of the shaft body and connected to the other ends of the first links, and a second extension extending from the other end of the shaft body in a direction crossing the longitudinal direction of the shaft body and connected to the other ends of the second links, and the needle is elongated in the longitudinal direction of the shaft body and is inserted into the shaft body, and wherein a diameter of each of the first and second extensions is smaller than a diameter of the frame.

3. The needle-coupled parallel mechanism of claim 2, wherein the needle is inserted into the main shaft.

4. The needle-coupled parallel mechanism of claim 3, wherein one end of the needle protrudes outwardly from the main shaft when the needle is moved linearly in one direction and is embedded within the main shaft when the needle is moved linearly in the opposite direction.

5. The needle-coupled parallel mechanism of claim 2, wherein the needle is elongated in one direction, has a sharp tip and is inserted into a living body to sample a living tissue.

6. The needle-coupled parallel mechanism of claim 2, wherein the needle is formed so as to have a hollow through which a drug supplied from the outside is injected into a living body after it is inserted into the living body.

7. The needle-coupled parallel mechanism of claim 2, wherein the needle is elongated in one direction and has a sharp tip so as to be inserted into a living body and applies an externally supplied current to a particular site of the living body therethrough.

8. The needle-coupled parallel mechanism of claim 2, wherein the three points at which the first links are connected to the frame, the three points at which the second links are connected to the frame, the three points at which the first links are connected to the one of the opposing ends of the main shaft, and the three points at which the second links are connected to the other of the opposing ends of the main shaft are in the form of regular triangles parallel to each other.

9. The needle-coupled parallel mechanism of claim 2, wherein the three points at which the first links are connected to the frame are arranged at equal intervals on the same circumference in the circumferential direction to form a regular triangle, the three points at which the second links are connected to the frame are arranged at equal intervals between the three points at which the first links are connected to the frame in the circumferential direction to form a regular triangle, the three points at which the first links are connected to the first extension of the main shaft are arranged at equal intervals on the same circumference in the circumferential direction to form a regular triangle, the three points at which the second links are connected to the second extension of the main shaft are arranged at equal intervals on the same circumference in the circumferential direction to form a regular triangle, and the plane including the three points at which the first links are connected to the first extension is parallel to the plane including the three points at which the second links are connected to the second extension.

10. The needle-coupled parallel mechanism of claim 2, wherein each of the first links and the second links consists of a 2-axis revolute joint, a prismatic joint and a spherical joint connected in this order from one end thereof, and the prismatic joint provides a driving force necessary to control the position and posture of the main shaft.

* * * * *